(12) United States Patent
Kaemper et al.

(10) Patent No.: US 8,746,244 B2
(45) Date of Patent: Jun. 10, 2014

(54) POWDER INHALER

(75) Inventors: Markus Kaemper, Breckerfeld (DE); Joern-Eric Schulz, Muenster (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 842 days.

(21) Appl. No.: 12/893,270

(22) Filed: Sep. 29, 2010

(65) Prior Publication Data

US 2011/0232637 A1   Sep. 29, 2011

(30) Foreign Application Priority Data

Oct. 2, 2009   (EP) .................................... 09172107

(51) Int. Cl.
*A61M 15/00*   (2006.01)
(52) U.S. Cl.
USPC ............ 128/203.21; 128/203.12; 128/203.15; 128/203.23
(58) Field of Classification Search
USPC ............. 128/203.12, 203.15, 203.21, 203.23, 128/203.24; 221/151, 152, 154, 197; 222/87–89, 153.13, 325
See application file for complete search history.

(56) References Cited

U.S. PATENT DOCUMENTS

| | | | |
|---|---|---|---|
| 2,946,332 A | | 7/1960 | Sacks |
| 4,338,931 A | | 7/1982 | Cavazza |
| 5,685,294 A | * | 11/1997 | Gupte et al. ............. 128/203.15 |
| 5,715,811 A | * | 2/1998 | Ohki et al. ............... 128/203.21 |
| 5,947,118 A | * | 9/1999 | Hochrainer et al. ...... 128/203.15 |
| 7,252,087 B2 | * | 8/2007 | Wachtel .................... 128/203.21 |
| 2006/0118106 A1 | * | 6/2006 | Schuckmann ........... 128/200.14 |
| 2006/0254584 A1 | * | 11/2006 | Wachtel .................... 128/203.19 |
| 2009/0277446 A1 | * | 11/2009 | Walz ......................... 128/203.15 |
| 2010/0275917 A1 | | 11/2010 | Kuhn et al. |
| 2011/0232637 A1 | | 9/2011 | Kaemper et al. |
| 2013/0098362 A1 | * | 4/2013 | Djupesland et al. ..... 128/203.15 |

FOREIGN PATENT DOCUMENTS

| | | |
|---|---|---|
| FR | 2352556 A1 | 12/1977 |
| WO | 2007118801 A1 | 10/2007 |
| WO | 2008065403 A2 | 6/2008 |
| WO | 2011039307 A2 | 4/2011 |

OTHER PUBLICATIONS

International Search Report and Written Opinion for PCT/EP2010/064562 mailed Apr. 4, 2011.

* cited by examiner

*Primary Examiner* — Justine Yu
*Assistant Examiner* — Timothy Stanis
(74) *Attorney, Agent, or Firm* — Michael P. Morris; Mary-Ellen M. Devlin

(57) ABSTRACT

Inhaler for inhaling powdered medicaments from capsules, comprising
 a lower part (6),
 a plate (3) accommodated in the lower part (6), and a holder (18) inserted in the lower part (6),
 a mouthpiece (2) that can be latched to the lower part (6) on the plate (3),
 a cover (1) that covers the mouthpiece (2) in a closed position and latches by means of a closure element (14), the lower part (6) and the cover (1) being rotatably (4) connected to one another by a spindle (4), and
 an actuating member (7, 10) that can be moved from a resting position and set in motion and at the same time co-operates with at least one pin (8, 11) that can be stuck into the holder (18) and is located in a pin holder in the inner actuating member (10).
In the holder (18) an exchangeable tube (22) can be inserted, as expulsion channel, which comprises a capsule chamber (21) with the capsule.

19 Claims, 3 Drawing Sheets

POWDER INHALER

The invention relates to an inhaler according to the pre-characterising clause of claim 1.

An inhaler known from the prior art is described for example in EP 0703800 B1 or EP 0911047 A1. The inhaler known from the above-mentioned publications has a dish-shaped lower part and a matching, equally dish-shaped lid which can be folded open for use by means of a hinge provided in the edge region. Between the lower part and lid, in the hinge, there is also a mouthpiece that can be folded away and a plate arranged below it with a capsule holder arranged underneath. After the individual assemblies have been flipped apart the patient can insert a drug-filled capsule in the capsule holder, pivot the plate with the capsule holder and the mouthpiece back into the lower part and pierce the capsule by means of a spring-loaded actuating member projecting laterally from the lower part. The medicament is then taken into the airways of the patient being treated by suction on the mouthpiece.

The aim of the invention is to improve the inhaler known from the prior art still further in terms of its handling.

This aim is achieved according to the invention with an inhaler having the features of claim 1 and an exchangeable tube for an inhaler according to claim 18.

The subclaims represent advantageous embodiments of the invention.

The inhaler for inhaling powdered medicaments from capsules comprises
- a lower part,
- a plate accommodated in the lower part, and a holder inserted in the lower part,
- a mouthpiece that can be latched to the lower part on the plate,
- a cover that covers the mouthpiece in a closed position and latches by means of a closure element, the lower part and the cover being rotatably connected to one another by a spindle, and
- an actuating member that can be moved from a resting position and set in motion and at the same time co-operates with at least one pin that can be stuck into the holder and is located in a pin holder in the inner actuating member.

In the holder, an exchangeable tube, as expulsion channel, can be inserted which comprises a capsule chamber with the capsule.

As a result of these measures, the operability of the inhaler is improved for inhaling powered medicaments from capsules, as prior to the use of the inhaler the capsule together with the exchangeable tube in the form of a disposable part that forms an expulsion channel for the powder is inserted directly into the holder arranged in the inhaler.

This results in easier handling for the user, as patients with reduced or poor grip in their hands find it easier, thanks to the size, to insert the exchangeable tube with the capsule contained therein than to place a capsule separately in a capsule chamber, as taught in the prior art. Moreover, after the nebulisation or inhalation, all the components of the inhaler that are noticeably affected by powder are replaced so that the next time the inhaler is used a new exchangeable tube, i.e., an unused expulsion channel is provided.

The new exchangeable tube also has an advantage with medicament formulations that have a tendency to form deposits in the powder expulsion pathway, as there are naturally no deposits in an unused expulsion channel caused by prior use of the inhaler.

The exchangeable tubes each containing at least one capsule may be taken by the patient from any packaging that is available according to the current state of the art (e.g. a blister pack, pouched or unpouched cartons or containers or individual pouches). Depending on the physical properties of the medicament that is to be inhaled, the skilled man will select the appropriate packaging for the exchangeable tube.

The inhaler corresponds in its function, particularly in terms of inhalation, i.e. the flow path of the powdered medicament, to the inhaler described in WO 2009/013218, which is hereby incorporated by reference. This applies particularly to the piercing process.

The inhaler consists essentially of an upper part formed by the mouthpiece which is protected by a cover, and a cup-shaped two-part lower part.

In the inner region of the cover is a cross piece, as known from WO 2009/013218. By means of this cross piece, on the inhaler according to the invention, it is not the mouthpiece but the exchangeable tube that is pressed into the end position when the cover is closed. Moreover, the cover has a bead that runs inwardly and outwardly and is not externally visible. This bead serves to close the cover on the actuating member which is located on the lower part of the inhaler.

In order to enable the cover to be detached from the lower part, the actuating member has on its upper side a recess which is inclined so that it forms a sliding surface for the closure element, in the form of a sloping plane, and when actuated and hence when the actuating member is advanced, releases the cover from the lower part. This function is only possible when the exchangeable tube is fully inserted. The recess in the actuating member may be of various sizes. The minimum size must be such that it is possible to release the cover from the lower part in a manner of a pocket watch. Its maximum size depends on the top of the actuating member. The actual opening movement of the cover can then be carried out by the patient, acting on the cover, and folding the cover fully open. Besides the release of the latch by the actuating member, by a suitable choice of size for the recess on the actuating member and the bead on the cover, the retaining force can also be overcome manually by the patient by pulling the cover manually over the catch without actuating any further elements.

In one embodiment, to assist the opening movement, a spring element, for example, may be arranged between the cover and/or the lower part, which is particularly in the form of two dishes, so that when the dimensions are suitable the cover snaps open. Alternatively, it is also obviously possible to have an embodiment of the inhaler without a spring element between the cover and the lower part. The cover can then spring open by a suitable choice of bead.

The actuating member is of greater importance, particularly at the onset of an asthma attack. The effective arrangement of the actuating member combined with a reduced application of force on the part of the patient makes the use of the inhaler considerably easier. This is particularly true for patients suffering from arthritis or similar diseases or having reduced mobility of their fingers for some other reason.

The actuating member consists of two components, and comprises an inner part and an outer part. The inner part has two parallel guide arms. The guide arms project into the lower part and together with corresponding inserts, for example with guide webs or sleeves arranged on the outside of the holder or on the inside of the halves of the lower part, they serve to guide the actuating member during the movement from the resting position to the respective operational positions and back into the resting position. Preferably, the actuating member comprises fixing elements, e.g. in the form of snap-fit hooks which ensure both secure assembly and robust operation of the device as a whole. The pivotably mounted outer part of the actuating member, when actuated, presses by means of a rounded contact surface on to the inner part which then moves in a linear manner to stick the pins into the capsule. The contact surface may be formed both on the inner part and on the outer part, but preferably only on the inner part.

The actuating member is connected to the lower part or to both halves of the lower part. This may be achieved by means of snap-fit hooks, latching hooks or similar technical solutions. Moreover, the actuating member may be movably mounted between the halves of the lower part in free space.

Preferably, the actuating member is movably mounted on the lower part or on the holder. It is also possible to mount it on the mouthpiece. The halves of the lower part or the lower part comprise or comprises preferably laterally mounted guide webs which are, however, also located on the plate and can be supported in the lower part or in the side dishes of the lower part.

In a favourable embodiment the actuating member is spring-loaded. The restoring force present even in the resting position ensures that after the actuating member has been used it is returned to the resting position and thus the inhalation process can be begun or continued. The guide arms may have end stops at their end remote from the main body, these stops bearing on the holder or on the guide sleeves in the resting position. This creates a reproducible spring tension on the actuating member which ensures that all the necessary components are precisely positioned in the operational position. The guide arms may be of any desired shape and arrangement (e.g. converging or diverging). Furthermore, it is possible to have one or more than two guide arms. The construction may be based on a round shape in cross section or of any desired profile.

In all, the actuating member has at least one abutment region which may be provided as desired on the inner or outer pressing part. In a preferred embodiment the main body of the actuating member may have at least one grooved surface on the outside. This grooved surface may be on the top, bottom or sides. Preferably, the grooved surface will be in at least one handhold on the actuating member. The grooved surface acts both as a design element and to ensure optimum grip during actuation. It is located on the main body of the actuating member outside the inhalation region and consequently does not come into contact with the patient's mouth region. Furthermore, the grooved surface may be smaller in area than the total surface area of the actuating member and still offers a guarantee of reliable and rapid use of the inhaler. Moreover, it is of course possible to provide the lower part and/or the cover with grooved surfaces as well to improve the handling of the inhaler still further.

For a better understanding of the invention it will now be described in more detail with reference to the following drawings, wherein.

Figure 1:
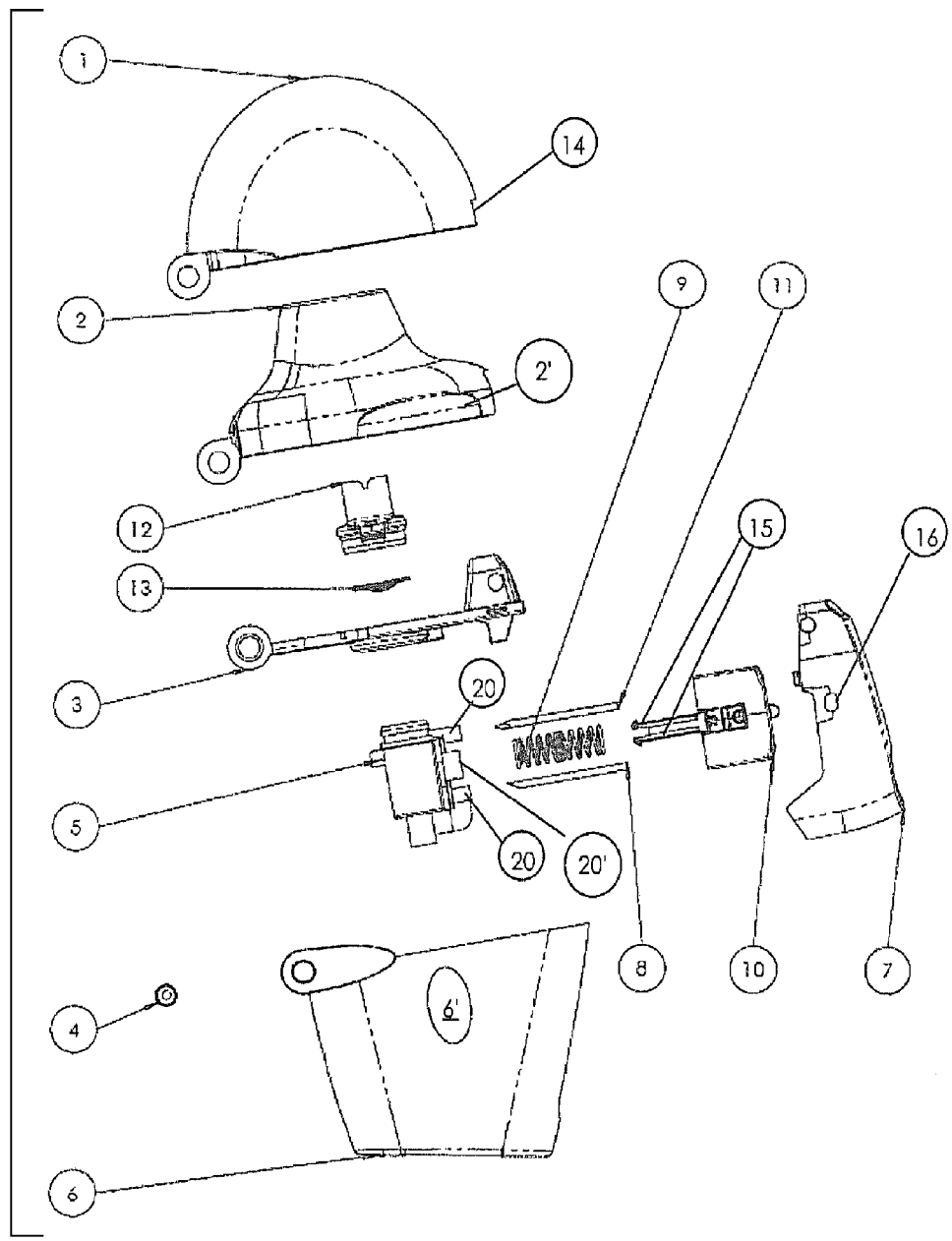
FIG. 1 shows an exploded view of an inhaler according to the prior art.

FIG. 1 shows an inhaler from the prior art. The essential components of the inhaler are a lower part 6 which accommodates a plate 3 and is covered by this plate, a mouthpiece 2 that can be latched to the plate 3 via retaining lugs of a screen housing 12 and a cover 1 which is designed to be complementary to the lower part 6. The plate 3, the lower part 6, the mouthpiece 2 and the cover 1 are mounted on a spindle 4.

In the closed state of the inhaler, a closure element 14 on the cover 1 engages on an outer actuating member 7 and is frictionally held thereon. It is also possible to provide an interlocking engagement by means of bead-like formations on the closure element 14. For the closure element 14 to act on the cover 1, the outer actuating member 7 comprises a recess into which the closure element 14 is lowered during the closing operation.

The actuating member consists of the outer actuating member 7 and an inner actuating member 10. In order to open the cover 1, first of all the outer actuating member 7 can be moved or pressed in the direction of the inhaler. The closure element 14 on the cover 1 meanwhile makes contact with the recess which, as the closure element 14 advances further, acts as a sliding surface and ensures that the cover 1 is released. Similarly, the cover 1 can be manually raised by the user without pressing on the actuating member 7 and in this way the inhaler can be opened.

The recess 16 connects the external and inner actuating members 7, 10 by means of a suspension which may take the form of a snap fit hook, pin or other suspending means, for example. The recess 16 may be round, oval or asymmetric in shape. The recess 16 may be arranged in a horizontal or vertical position or in any position. Preferably, the recess 16 is a so-called oblong hole, i.e. an elongate oval which provides optimum guidance of the pins in the axial direction to ensure accurate piercing of the capsule.

The lower part 6 is cup-shaped and fully accommodates a capsule holder 5 arranged on the underside of the plate 3. In order to be able to place a drug-filled capsule (not shown) in the capsule holder 5, the mouthpiece 2 also has to be flipped out of the way. In the embodiment according to FIG. 1 this is done by actuating the opening aid 2' which is provided on the mouthpiece 2.

In this opened position of the cover 1 and mouthpiece 2 the capsule can be placed in the capsule holder 5 through an opening in the plate 3. The mouthpiece 2 is then pivoted back again and by latching the retaining lugs of the screen housing 12 which is frictionally connected to the mouthpiece in the plate 3 it is closed off again. The screen housing 12 contains the screen mesh 13 in its centre. The screen mesh 13 consists of standard commercial materials such as metal or plastics, for example. In the latter case the screen may be produced by extrusion moulding. To release the active substance the outer actuating member 7 is operated. It is designed so that the pin holder is above the point of application of the force and below the suspension for the operating key. On the inner actuating member 10 is at least one pin, but preferably two, perpendicularly offset and parallel pins 8, 11, which move continuously as the actuating member 7, 10 is pushed in the direction of the capsule (not shown) and perforate this capsule. The perforation process can be observed through an inspection window 6'.

In the capsule holder 5 are two tubular pin guides 20 which are aligned axially according to the direction of movement of the pins 8, 11. Thus provision is made for accurately targeted application of the pins 8, 11 to the capsule (not shown) on the one hand and for additional guide of the actuating member 7, 10, on the other hand. However, the essential guidance is provided by means of two laterally arranged guide sleeve 20'. Guide arms 15, in collaboration with the guide sleeves 20', have the task of holding the actuating member 7, 10 under a biasing force. For this, the guide arms 15 are provided with end stops at their ends remote from the main body, these end stops abutting on the guide sleeves of the capsule holder 5 in the resting position of the actuating member 7, 10. The guide sleeves are located on the outside of the capsule holder 5. Between the guide arms 15 a helical spring 9 is arranged which extends parallel to pins 8, 11 in its axial direction, the helical spring 9 being matched to the length of the guide arms 15 such that the actuating member 7, 10 is still biased in the resting position.

The individual assemblies comprising the lower part 6, the plate 3, the mouthpiece 2 and cover 1 are connected to one another via hinge recesses and a spindle 4 and are all pivotable relative to one another about this spindle 4.

Figure 2:
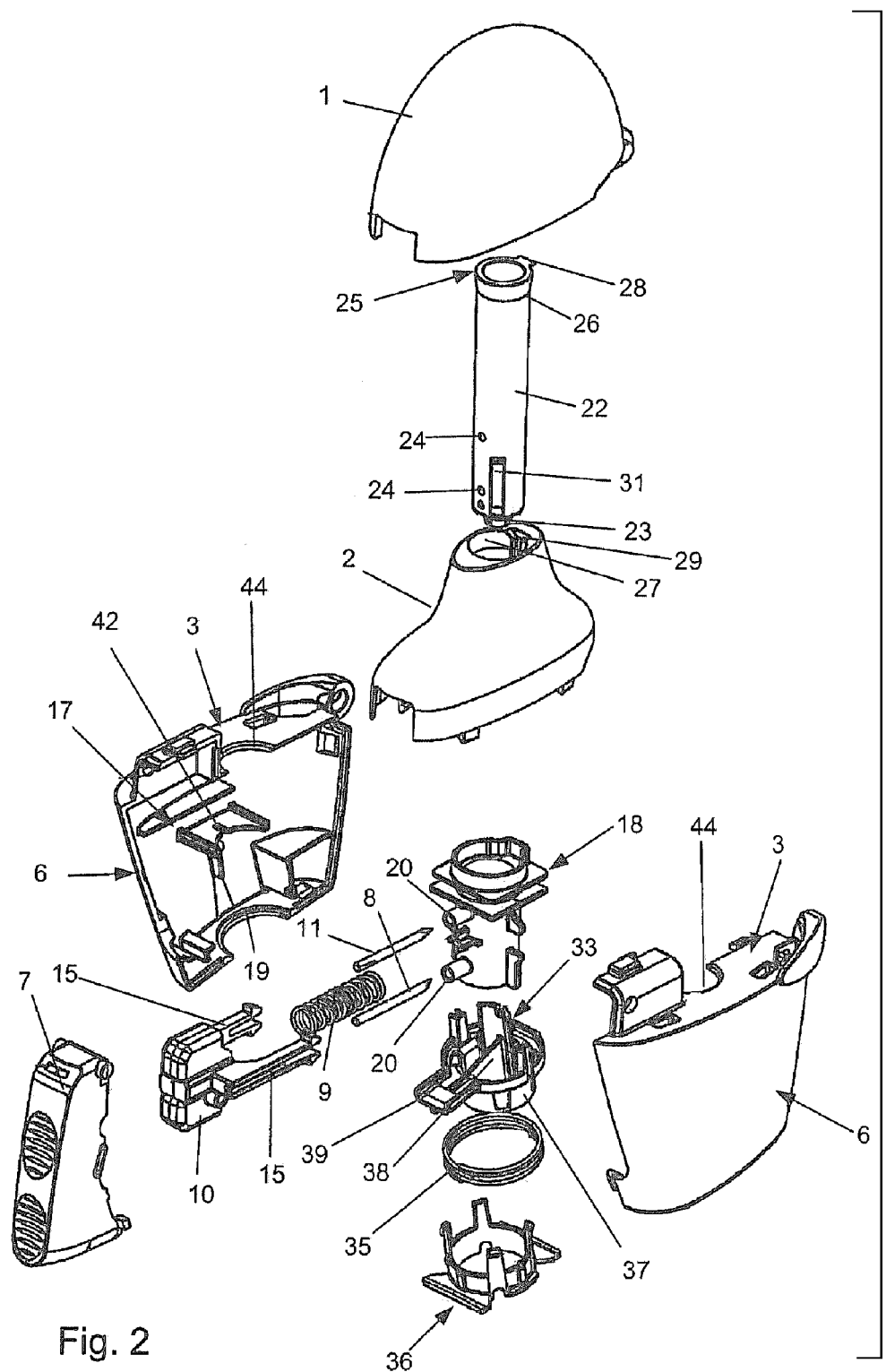
FIG. 2 shows an exploded view of an inhaler according to the invention.
Figure 3:
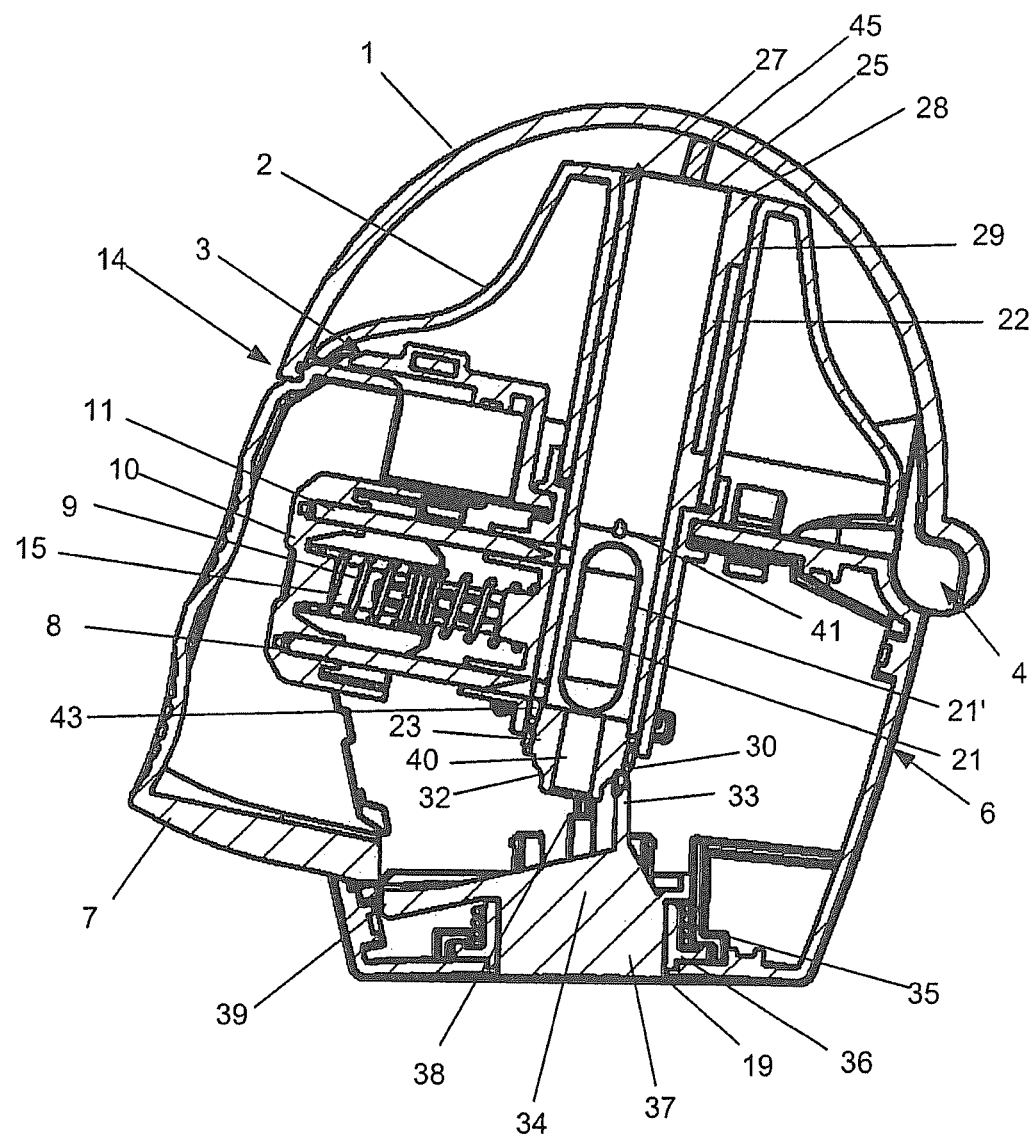
FIG. 3 shows a sectional view of the inhaler according to FIG. 2.

In the inhaler shown in FIGS. 2 and 3, in contrast to the inhaler described above, the lower part 6 is made in two parts and comprises the plate 3 as an integral component. In the lower part 6 are provided lateral retaining webs 17, each having a recess 42, for a holder 18 and an opening 19 in the base.

The holder 18 is provided with the two tubular pin guides 20 and is held by the retaining web 17 arranged in the lower part 6 with the recess 42 and the opening 44 in the two-part plate 3.

The capsule 21' with the medicament that is to be inhaled is located in a capsule chamber 21 in a so-called exchangeable tube 22 which is pushed into the inhaler through the mouthpiece 2 and the holder 18. The exchangeable tube 22 consists essentially of a plastic tube which is filled with the capsule from below and is closed off with a stopper 23 preferably also made of a plastic, the stopper 23 being provided with an axial bore 40 to form a flow channel. By the provision of a transfer member 41 injection moulded in the exchangeable tube 22 the capsule is prevented from falling out in the upward direction and the space it requires for vibrating during inhalation, i.e. the length of the capsule chamber, is determined. Preferably, the stopper 23 is a separate component which cannot be removed once it has been fitted to the exchangeable tube 22. On its underside the stopper 23 comprises functional slopes or surfaces 32 which can be used for ejecting the exchangeable tube 22. The upper part of the exchangeable tube 22 forms the entire air passage through which the nebulised powder formulation travels before it is breathed in by the patient using the inhaler.

Alternatively, the stopper 23 may also be fixedly moulded on the exchangeable tube 22 and the transverse member 41 may also be provided as a separately multiple component for introducing the capsule. Another alternative might be an exchangeable tube 22 injection moulded complete with stopper 23 and transverse member 41 which comprises a closable lateral opening for the introduction of the capsule. It is also possible to construct the exchangeable tube 22 in several parts.

The airway of the exchangeable tube 22 is adapted to inhalation of the active substances that are to be inhaled, so that compared with the inhaler from the prior art the internal diameter of the airway may be greater or smaller. In order to achieve the required provision of powder, the transverse member 41 forms both the necessary height of the capsule chamber 21 within the exchangeable tube 22 to allow the capsule to vibrate, and also presents an air resistance that is adapted to the active substance formulation.

After being pushed into the inhaler the exchangeable tube 22 ends flush with the mouthpiece 2 on its upper surface in the position of use, so that the user will not be able to detect a step. In this position the two tubular pin guides 20 of the holder 18 are in alignment with circumferential openings 24 for the pins 8, 11 in the exchangeable tube 22. It is also possible for part of the mouthpiece 2 even in the outer region to count as the exchangeable tube 22, so that the junction of the exchangeable tube 22 with the mouthpiece 2 may be at any desired point. This ensures that the exchangeable tube 22 is correctly inserted, a mechanism is integrated in the inhaler which prevents the actuating member 7, 10 from being actuated before the exchangeable tube 22 has assumed its correct end position, in order to pierce the capsule with the pins 8, 11. The actuating member 7, 10 can be blocked off such that no actuation at all is possible, i.e. the cover 1 cannot be opened, and preferably the closure element is designed so that the cover 1 can be opened if no exchangeable tube 22 has been inserted. Preferably, the position of the exchangeable tube 22 may be optically recognisable from a coloured marking on the upper region of the exchangeable tube 22. When the exchangeable tube 22 is correctly inserted in the end position the marking disappears with the mouthpiece 2 and is no longer visible. Moreover, the cover 1 that covers the mouthpiece 2 in a closed position has, in its interior, a crosspiece 45 which in the closed state of the cover, presses on the exchangeable tube 22 introduced therein and the mouthpiece.

So that the exchangeable tube 22 is correctly positioned in the inhaler, the exchangeable tube 22 comprises, in the region of its upper surface 25 associated with the mouthpiece 2, an insertion cone 26 which lies in a correspondingly shaped opening 27 in the mouthpiece 2 in the axial position of use of the exchangeable tube 22. To ensure the radial alignment of the exchangeable tube 22 as well, the exchangeable tube 22 is provided, in the region of its upper surface 25 associated with the mouthpiece 2, with a radially projecting lug 28 which has an associated corresponding groove 29 in the opening 27 of the mouthpiece 2. The combination of the lug 28 and groove 29 may also be used for active substance codings, if required, in suitable dimensions or geometries, so that an inhaler can only ever be operated with one active substance. Another idea that has been considered is that the exchangeable tube 22 should have different external diameters so that the upper end 25 cannot be inserted first.

In the lower region of the exchangeable tube 22 is an annular groove 30, in this case circumferential in shape, which enters into a connection with the stopper 23. Furthermore, a radially acting latching hook 43 is releasably provided for holding the exchangeable tube 22 releasably in the inhaler by latching. The depression 31 needed for this may be circumferential, while alternatively the function may be performed by means of individual notches, webs or the like. It is also possible to provide at least one depression for latching the exchangeable tube 22 in the holder 18 and a latching hook on the exchangeable tube 22.

In another embodiment of the inhaler the openings 24 for the pins 8, 11 in the exchangeable tube 22 may be closed off by means of a membrane of the like. The membrane may be produced directly by injection moulding or produced by special methods using the same or a different plastics component as the exchangeable tube 22. The membrane wipes away powder adhering to the pins 8, 11 after the piercing of the capsule, as the pins 8, 11 slide out of the capsule chamber 21, so that the pins 8, 11 are clean for the next use. This enables pins 8, 11 to be used many times for piercing capsules containing powder formulations.

The chamber wall may be both a wall region of the capsule chamber 21, i.e. of the exchangeable tube 22, and a membrane in the region of the pin guide 20. In principle, the same membrane can certainly be used many times as even after the removal of the pin it is sufficiently well sealed towards the side remote from the capsule and is still leaktight even after being pierced a number of times. The principle can be transferred to all common pin shapes, both hollow and solid pins. For the membrane it is possible to use both identical and different materials or material combinations and geometries, such as e.g. their thickness, for adjusting the flexibility (solutions in a material with variations in layer thickness are also possible), and it is possible to use both any kind of plastic that is hard or soft at ambient temperature such as for example TPEs, thermoplasts, rubbers and also materials consisting of other (inorganic) groups such as thin metal films, etc.

When a capsule with a membrane in front of it is pierced, the membrane bulges towards the capsule end as it is pierced before the pin actually passes through; the membrane may be the chamber wall or may be directly connected to the chamber wall—either by conventional injection moulding or by 2-component injection moulding techniques or by assembly from two or more parts. The attachment of the membrane may be achieved in any desired manner: moulded on or extrusion-coated, clipped on, inserted, glued with additional material or for example by the self-sticking effects of the membrane material, etc. Alternatively, the wiping off of the tacky powder may also be carried out on a close-fitting or flexible sleeve through which the pin 8, 11 is passed.

As the exchangeable tube 22 is inserted in the inhaler it first latches movably in an inserted intermediate position. As it is inserted further, a slightly increased resistance has to be overcome so that the exchangeable tube 22 takes up its releasably latched position of use. The resistance is caused by the fact that the latching hook 43 acting on the exchangeable tube 22 is moulded on the holder 18.

Interlockingly engaged underneath the stopper 23 is a latching hook 33 located on the slope 32 on one side or all round it. The latching hook 33 is integrated in an intermediate ring 34 and is movably secured in the lower part 6 by means of a compression spring 35 and a retaining ring 36. The intermediate ring 34 has a coaxial actuating button 37 which passes through the retaining ring 36 and the opening 19 in the lower part 6 for actuation by a user in order to release the latch.

Once the exchangeable tube 22 with the capsule has been pushed into the inhaler (FIG. 3) nebulisation takes place as in the previous inhaler. By means of the actuating member 7, 10 which can be actuated with one or more fingers simultaneously, the capsule is pierced, through the corresponding openings 24 in the exchangeable tube 22, by two pins 8, 11 at the top and bottom. The exchangeable tube 22 is installed in an oriented position in the inhaler so that the pins 8, 11 are actually able to penetrate into the corresponding openings 24 in the exchangeable tube 22. The helical spring 9 in the actuating member 7, 10 ensures that the pins 8, 11 are automatically retracted from the capsule as soon as the actuating member 7, 10 is released. Inhalation takes place according to the tried and tested principle by vibration of the capsule in the intake of breath by the patient as the latter sucks on the mouthpiece 2.

After the inhalation, the exchangeable tube 22 with the now empty capsule in the capsule chamber 21 is released by pressing on the actuating button 37, which in this embodiment is spring-assisted, in the base of the inhaler, i.e. on the opposite side from the mouthpiece 2. This actuating button 37 is interlockingly connected to the stopper 23 by means of its integrated latching hook 33.

By means of the spring biasing of the intermediate ring 34, the clamping latching of the exchangeable tube 22 can be released, as the latching hook 43 moves out of engagement with the associated recess 31, and the exchangeable tube 22 is pressed upwards out of the inhaler. Depending on the design, solutions are possible in which the release of the exchangeable tube 22 is carried out without the assistance of a spring, purely by the use of a slider. What is important is that a retaining function for the exchangeable tube 22 in the intermediate position is integrated therein, which has to be released deliberately, e.g. using a key or button, before the exchangeable tube 22 can be removed manually from the inhaler by pulling it over the latching hook 43. Spring-free mechanisms or mechanisms that only partly eject the exchangeable tube 22 are also possible. Another possibility here is to implement a secondary retaining threshold in the intermediate position which holds the exchangeable tube 22 back after it has been ejected in a position protruding from the mouthpiece 2, from which it can then be pulled out manually.

If the exchangeable tube 22 has either just been ejected or a new exchangeable tube 22 has not been pushed right in as far as the end stop, a radial bar 39 moulded on the intermediate ring 34 underneath the lower part 6 comes into effect. As a result of the action of the compression spring 35 from inside, the bar 39 comes into contact with the outer actuating member 7 so that its operation is impeded. The bar 39 blocks the outer actuating member 7 with its free end if either there is no exchangeable tube 22 present or if the exchangeable tube 22 is not occupying the latched position of use. In this position, the pins 8, 11 cannot move inwards, i.e. cannot be damaged by an exchangeable tube 22 that has not been fully inserted.

This ensures that the pins 8, 11 always penetrate into the openings 24 in the exchangeable tube 22 that has been inserted in the required orientation and do not, for example, block off the insertion opening for the exchangeable tube 22 and/or become damaged. As the exchangeable tube 22 is pushed into its latched position of use, the intermediate ring 34 is pushed downwards over its upwardly pointing sloping web 38 and the action of the stopper 23 on the latching hook 33 counter to the force of the compression spring 35, so that the bar 39 is moved out of the pivot path of the outer actuating member 7. At the same time, the actuating button 37 returns to ejection readiness, i.e. it assumes an ideally flush position with the lower part 6 and can be reached by the user of the inhaler.

The pins 8, 11 used may be any pins 8, 11 known to the skilled man and combinations thereof. They may be solid or hollow pins. Preferably, solid pins are used. The upper pin, in particular, (facing the mouthpiece) may be a triangular pin sharpened on three sides. The lower pin may be a standard pin with a standard sharp edge, as specified for example in the German DIN standard. Alternatively, the upper pin 11 may be a standard pin with a standard sharp edge and the lower pin 8 may be a triangular pin sharpened on three sides. As a second alternative it is possible to use two triangular pins sharpened on three sides or two standard pins with a standard sharp edge.

The capsules used may be any capsules known to the skilled man for use in powder inhalers (e.g. (hard) gelatine, plastic or metal capsules). In particular a plastic capsule may be used in the inhaler according to the invention, as disclosed in WO 00/07572, EP 1 100 474.

The inhaler may have an inspection window. However, this is not essential for its intended function.

Similarly, all the parts of the inhaler may be modified by methods known to the skilled man and procedures that are possible in plastics technology. Possible modifications include for example reinforcements or variations in the wall thickness. These possibilities are not, however, strictly necessary for the operation of the inhaler.

The inhaler may also be coated on its interior and/or exterior by methods known to the skilled man.

All kinds of powdered medicaments which may reasonably be administered by inhalation for therapeutic purposes may be considered for the inhalation.

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1-dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)phenyl]-formamide 8-hydroxy-5-(1-hydroxy-2-{2-[4-(6-methoxy-biphenyl-3-ylamino)-phenyl]-ethylamino}ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxy-ethyl)-2-hydroxymethyl-phenol N-adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

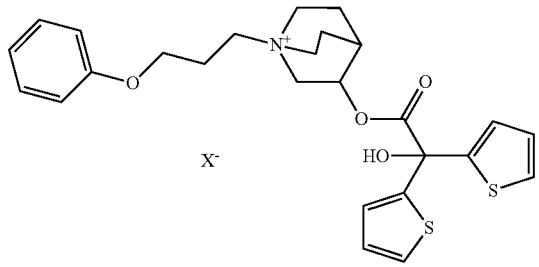

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-ene

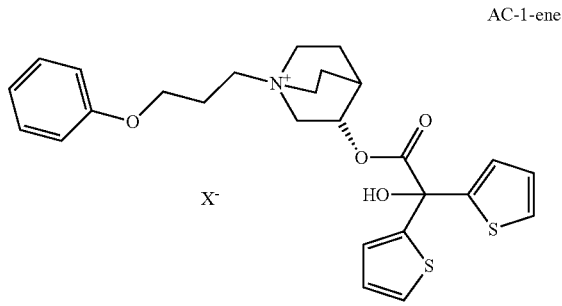

AC-1-ene wherein X⁻ may have the above-mentioned meanings. Other preferred anticholinergics are selected from the salts of formula AC-2

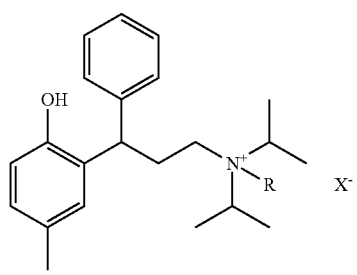

AC-2 wherein R denotes either methyl or ethyl and wherein X⁻ may have the above-mentioned meanings. In an alternative embodiment the compound of formula AC-2 may also be present in the form of the free base AC-2-base.

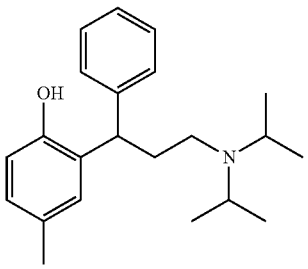

AC-2-base

Other specified compounds are:
tropenol 2,2-diphenylpropionate methobromide
scopine 2,2-diphenylpropionate methobromide
scopine 2-fluoro-2,2-diphenylacetate methobromide
tropenol 2-fluoro-2,2-diphenylacetate methobromide
tropenol 3,3',4,4'-tetrafluorobenzilate methobromide
scopine 3,3',4,4'-tetrafluorobenzilate methobromide
tropenol 4,4'-difluorobenzilate methobromide
scopine 4,4'-difluorobenzilate methobromide
tropenol 3,3'-difluorobenzilate methobromide
scopine 3,3'-difluorobenzilate methobromide
tropenol 9-hydroxy-fluorene-9-carboxylate methobromide
tropenol 9-fluoro-fluorene-9-carboxylate methobromide
scopine 9-hydroxy-fluorene-9-carboxylate methobromide
scopine 9-fluoro-fluorene-9-carboxylate methobromide
tropenol 9-methyl-fluorene-9-carboxylate methobromide
scopine 9-methyl-fluorene-9-carboxylate methobromide
cyclopropyltropine benzilate methobromide;
cyclopropyltropine 2,2-diphenylpropionate methobromide
cyclopropyltropine 9-hydroxy-xanthene-9-carboxylate methobromide
cyclopropyltropine 9-methyl-fluorene-9-carboxylate methobromide
cyclopropyltropine 9-methyl-xanthene-9-carboxylate methobromide
cyclopropyltropine 9-hydroxy-fluorene-9-carboxylate methobromide
cyclopropyltropine methyl 4,4'-difluorobenzilate methobromide
tropenol 9-hydroxy-xanthene-9-carboxylate methobromide
scopine 9-hydroxy-xanthene-9-carboxylate methobromide
tropenol 9-methyl-xanthene-9-carboxylate methobromide
scopine 9-methyl-xanthene-9-carboxylate methobromide
tropenol 9-ethyl-xanthene-9-carboxylate methobromide
tropenol 9-difluoromethyl-xanthene-9-carboxylate methobromide
scopine 9-hydroxymethyl-xanthene-9-carboxylate methobromide The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-5-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the PDE4 inhibitors are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention these acid addition salts are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]-amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxyethyl)-amino]-1-oxo-2-buten-1-yl]amino}-7-cyclopropylmethoxy-quinazoline 4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxyethyl)-N-methyl-amino]1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino-cyclohexan-1-yloxy}-7-methoxy-quinazoline 4-[(3-chloro-4-fluoro-phenyl)amino]-6-{trans-4-[(morpholin-4-yl)sulphonylamino-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonyl-methyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline
optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The pharmaceutically effective substances, formulations or mixtures of substances used may be any inhalable compounds, including also for example inhalable macromolecules, as disclosed in EP 1 003 478. Preferably, substances, formulations or mixtures of substances for treating respiratory complaints which are administered by inhalation are used.

In addition, the compound may come from the group of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

| List of reference numerals | |
|---|---|
| 1. | cover |
| 2. | mouthpiece |
| 2'. | opening aid |
| 3. | plate |
| 4. | spindle |
| 5. | capsule holder |
| 6. | lower part |
| 6'. | inspection window |
| 7. | outer actuating member |
| 8. | pin |
| 9. | helical spring |
| 10. | inner actuating member |
| 11. | pin |
| 12. | screen housing |
| 13. | screen mesh |

-continued

List of reference numerals

| | |
|---|---|
| 14. | closure element |
| 15. | guide arm |
| 16. | recess |
| 17. | retaining webs |
| 18. | holder |
| 19. | opening of 6 |
| 20. | pin guide |
| 20'. | guide sleeve |
| 21. | capsule chamber |
| 21'. | capsule |
| 22. | exchangeable tube |
| 23. | stopper |
| 24. | opening of 22 |
| 25. | top of 22 |
| 26. | insertion cone |
| 27. | opening of 2 |
| 28. | lug |
| 29. | groove |
| 30. | annular groove |
| 31. | depression |
| 32. | slope of 23 |
| 33. | latching hook of 37 |
| 34. | intermediate ring |
| 35. | compression spring |
| 36. | retaining ring |
| 37. | actuating button |
| 38. | crosspiece of 34 |
| 39. | bar |
| 40. | axial bore |
| 41. | transverse member |
| 42. | recess |
| 43. | latching hook of 23 |
| 44. | opening of 3 |
| 45. | crosspiece |

What is claimed is:

1. An inhaler for inhaling powdered medicaments from capsules, comprising:
    a lower part (6),
    a plate (3) accommodated in the lower part (6),
    a holder (18) disposed in the lower part (6),
    a mouthpiece (2) that is latchable to the lower part (6) on the plate (3),
    a cover (1) that covers the mouthpiece (2) in a closed position of the cover (1), and
    an actuating member (7, 10) that is movable from a resting position and set in motion and at the same time co-operates with at least one pin (8, 11), such that the pin is stuck into the holder (18), where the pin is located in a pin holder in the inner actuating member (10),
    wherein, as an expulsion channel, an exchangeable tube (22) is insertable into the inhaler by pushing the exchangeable tube (22) through the mouthpiece (2) and into the holder (18), the exchangeable tube (22) comprising a capsule chamber (21) with a capsule, and being releasably latched in the inhaler in its position of use and extending through the mouthpiece.

2. The inhaler according to claim 1, wherein the exchangeable tube (22) with the capsule may be used for a single inhalation.

3. The inhaler according to claim 1, wherein the inhaler has a locking device for holding the exchangeable tube (22) in its axial position of use, the locking device comprising at least one latching hook (43) which engages in an associated recess (31) on the exchangeable tube (22).

4. The inhaler according to claim 3, wherein a radial bar (39) is formed on a resiliently mounted intermediate ring (34), said bar cooperating with the actuating member (7, 10) such that, when no exchangeable tube (22) is present, or no exchangeable tube (22) is secured in the axial position of use, the bar secures the actuating member (7, 10) so as to prevent the actuating member (7, 10) from moving to pierce the capsule, and when an exchangeable tube (22) is secured in the axial position of use, the bar (39) releases the actuating member (7, 10) to pierce the capsule with the pins.

5. The inhaler according to claim 4, wherein the intermediate ring (34) is guided in an axially movable manner, via an interposed compression spring (35), on a retaining ring (36) which is secured at a base thereof in the lower part (6).

6. The inhaler according to claim 5, wherein the intermediate ring (34) has a coaxial actuating button (37) for actuation by a user in order to release the latch wherein the actuating button (37) projects through the retaining ring (36) and an opening (19) in the lower part.

7. The inhaler according to claim 6, wherein the lower part (6) is in the form of two dish shapes.

8. The inhaler according to claim 3, wherein the latching hook (43) is radially acting and holds the exchangeable tube (22) releasably in the inhaler by latching, the exchangeable tube having for this purpose a depression (31) in which the latching hook (43) engages.

9. The inhaler according to claim 1, wherein the capsule chamber (21) is bounded on one side of the capsule chamber (21) by a stopper (23) and on another side by a transverse member (41) projecting into the exchangeable tube (22).

10. The inhaler according to claim 1, wherein the inhaler comprises an opening (27) in the mouthpiece (2), wherein the exchangeable tube (22) is insertable into the inhaler by pushing the exchangeable tube (22) into the opening (27), and the exchangeable tube (22) comprises a radially projecting lug (28) in the region of an upper side (25) of the tube (22), wherein the upper side (25) is associated with the mouthpiece (2), and wherein a corresponding groove (29) in the opening (27) of the mouthpiece (2) is associated with the radially projecting lug (28).

11. The inhaler according to claim 1, wherein the exchangeable tube (22) is provided with an insertion cone (26), in the region of an upper side (25) of the tube (22), wherein the upper side (25) is associated with the mouthpiece (2), wherein the insertion cone (26) lies in a correspondingly shaped opening (27) in the mouthpiece (2) in the axial position of use of the exchangeable tube (22).

12. The inhaler according to claim 1, wherein the exchangeable tube (22) is movably latched in an inserted intermediate position between a position of use and the removal of the tube (22), wherein in the intermediate position the exchangeable tube (22) protrudes from the mouthpiece (2).

13. The inhaler according to claim 1, wherein the capsule chamber (21) is of suitable dimensions and shape for receiving a plurality of capsules, where the capsules are pieced by corresponding pins (8, 11).

14. The inhaler according to claim 1, wherein the outer actuating member (7) is blocked to prevent the actuation member from being depressed if the exchangeable tube (22) is not correctly inserted.

15. The inhaler according to claim 1, wherein after being pushed into the inhaler, the exchangeable tube (22) ends flush with the mouthpiece (2) on an upper surface thereof in the position of use.

16. An inhaler for inhaling powdered medicaments from capsules, comprising
    a lower part (6),
    a plate (3) accommodated in the lower part (6),
    a holder (18) disposed in the lower part (6), a mouthpiece (2) that is latchable to the lower part (6) on the plate (3), a cover (1) that covers the mouthpiece (2) in a closed position of the cover (1), and an actuating member (7, 10) that is movable from a resting position and set in motion and at the same time cooperates with at least one pin (8, 11), such that the pin is stuck into the holder (18), where the pin is located in a pin holder in the inner actuating member (10), wherein, as an expulsion channel, an exchangeable tube (22) is insertable in the holder (18) and the exchangeable tube (22) comprises, on a circumferential side of the tube (22), openings (24) for the pins (8, 11), the openings (24) being closed off by a membrane.

17. The inhaler according to claim 16, wherein the exchangeable tube (22) has ends of different thicknesses to prevent incorrect insertion.

18. An inhaler for inhaling powdered medicaments from capsules, comprising a lower part (6), a plate (3) accommodated in the lower part (6), a holder (18) disposed in the lower part (6), a mouthpiece (2) that is latchable to the lower part (6) on the plate (3), a cover (1) that covers the mouthpiece (2) in a closed position of the cover (1), and an actuating member (7, 10) that is movable from a resting position and set in motion and at the same time cooperates with at least one pin (8, 11), such that the pin is stuck into the holder (18), where the pin is located in a pin holder in the inner actuating member (10), wherein, as an expulsion channel, an exchangeable tube (22) is insertable in the holder (18), the exchangeable tube (22) comprising a capsule chamber (21) with a capsule, and being actively released by operation of an actuating button (37) which projects through an opening (19) in the lower part (6).

19. The inhaler according to claim 18, wherein the actuating button (37) is on the side of the inhaler opposite the mouthpiece (2) and the exchangeable tube (22) which extends through the mouthpiece (2) is released by pressing the actuating button (37).

* * * * *